United States Patent [19]

Ford et al.

[11] 4,362,886
[45] Dec. 7, 1982

[54] PREPARATION OF LINEAR POLYALKYLENE POLYAMINES USING METAL CATALYST

[75] Inventors: Michael E. Ford, Trexlertown; Thomas A. Johnson, Orefield, both of Pa.

[73] Assignee: Air Products and Chemicals, Inc., Allentown, Pa.

[21] Appl. No.: 222,817

[22] Filed: Jan. 5, 1981

[51] Int. Cl.$^3$ .................. C07C 85/06; C07D 241/04; C07D 403/12
[52] U.S. Cl. .................................. 564/479; 544/359; 544/382
[58] Field of Search ...................... 564/479, 478, 402; 544/359, 382

[56] References Cited

U.S. PATENT DOCUMENTS

| | | | |
|---|---|---|---|
| 2,389,500 | 11/1945 | Goshorn | 564/479 X |
| 3,714,259 | 1/1973 | Lichtenwalter et al. | 564/512 X |
| 4,036,881 | 7/1977 | Brennan et al. | 564/512 X |

*Primary Examiner*—John Doll
*Attorney, Agent, or Firm*—Russell L. Brewer; E. Eugene Innis; James C. Simmons

[57] ABSTRACT

A process for selectively preparing predominantly non-cyclic polyalkylene polyamine compounds is disclosed wherein an alkylene polyamine compound is contacted with a hydroxy compound in the presence of a catalytically effective amount of a substance of arsenic, antimony or bismuth at a temperature of from 250° to 300° C. under a pressure sufficient to maintain the reaction mixture essentially in liquid phase. The polyalkylene polyamine thus formed is recovered from the reaction mixture.

8 Claims, No Drawings

PREPARATION OF LINEAR POLYALKYLENE POLYAMINES USING METAL CATALYST

TECHNICAL FIELD

This invention relates to the preparation of polyalkylene polyamines.

BACKGROUND OF PRIOR ART

One of the early techniques for preparing linear polyalkylene polyamine compounds, such as diethylenetriamine and triethylene tetramine and higher homologues, has been to react an alkyl halide with an amine such as ammonia, ethylenediamine and the like at elevated temperatures and pressures. Generally, high yields of cyclic polyethylene polyamines, e.g. piperazine, triethylenediamine as well as other cyclic amines were produced. Another problem in the process was that hydrohalide salts of ammonia or hydrogen chloride were produced by the reaction, and thus expensive corrosion resistant equipment was required. U.S. Pat. No. 3,751,474 is representative.

More recently a series of patents have issued which disclose the preparation of linear polyalkylene polyamine compounds by reacting a diol or an alkanolamine compound with an alkylenediamine compound under preselected process conditions to produce linear alkylene polyamines. These include:

U.S. Pat. No. 3,714,259, which shows preparing linear poly(ethylene)amines by contacting ethanolamine with an ethylenediamine compound in the presence of hydrogen and hydrogenation catalyst. An example of a hydrogenation catalyst is nickel containing copper and chromium components;

U.S. Pat. No. 4,036,881, which shows the preparation of polyalkylene polyamines by reacting an alkanolamine with an alkylene amine compound in the presence of a phosphorous-containing substance selected from the group consisting of acidic metal phosphates, phosphoric acid compounds and hydrides and phosphate esters; and U.S. Pat. No. 4,044,053, which is somewhat similar to the U.S. Pat. No. 4,036,881 patent except that the alkylene amine compound is present in an excess amount and a diol is used in place of the alkanolamine.

SUMMARY OF THE INVENTION

It has been found that non-cyclic or linear polyalkylene polyamines are produced in high yield directly by reacting an alkylene amine compound and an alkanolamine in the presence of a catalytically effective amount of a compound containing arsenic, bismuth or antimony at temperatures of from 250°–350° C. under a pressure sufficient to maintain the mixture in liquid phase.

DETAILED DESCRIPTION OF THE INVENTION

Briefly, the invention relates to a process for synthesizing predominantly non-cyclic polyalkylene polyamines, and preferably predominantly linear polyethylene polyamines such as diethylenetriamine and higher homologues. In the process an alkylene amine having two primary amino groups, and preferably an unbranched alkylene moiety such as ethylene diamine, is reacted with an alkanolamine having a primary or secondary hydroxy moiety and a primary amine group. Preferably, the alkanolamine has an unbranched alkylene moiety.

The alkylene amine reactants that can be used in practicing the process are represented by the general formula:

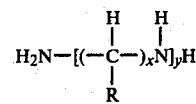

where R is a hydrogen or a lower alkyl ($C_{1-4}$) radical, X is a number from 2 to about 6, and Y is a number from 1 to about 4. Examples of alkylene diamine compounds suited for the reaction include 1,3-propylenediamine, piperazine, N-(2-aminoethyl)piperazine, diethylenetriamine, triethylenetetramine and ethylenediamine, which is the preferred alkylene diamine composition.

The alkanolamine compounds which are used in practicing the process include those represented by the formula:

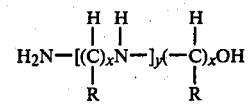

wherein R is hydrogen or a lower alkyl ($C_{1-4}$) radical; X is a number from 2 to about 6; and Y is a number from 0 to 3. Examples of alkanolamine compounds that can be used are ethanolamine, isomeric propanolamines, and N-(2-hydroxyethyl)piperazine.

The polyalkylene amines that are produced by the reaction of an alkylenediamine and an alkanolamine or diol then are represented by the formula:

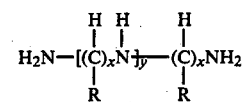

wherein R is hydrogen or a lower alkyl ($C_{1-4}$) radical; X is a number from 2 to about 6; and Y is a number from 2 to about 6. Examples of linear polyalkylene polyamines that are produced include tributylenetetramine, diethylenetriamine, triethylenetetramine and tetraethylenepentamine.

Virtually any antimony, bismuth or arsenic compound can be used, e.g. arsenic pentoxide, lead arsenate, bismuth nitrate, bismuth chloride, antimony (III) oxide, antimony (V) oxide, ammonium dihydrogen arsenate, bismuth oxide, phenyl arsenic acid, disodium hydrogen arsenate, sodium hydrogen arsenate, arsenic (III) chloride, arsenic trioxide, methyl arsenic acid, methylarsine dibromide, antimony (III) chloride, antimony (IV) chloride, antimony potassium tartrate, antimony sulfate, bismuth bromide, bismuth chloride oxide, bismuth nitrate oxide, bismuth titanate, bismuth zirconate, and the like.

The above-mentioned arsenic, bismuth or antimony-containing compounds are not intended to be exhaustive of those which may be employed as a catalyst material. However, as might be expected, it is preferred to use those which are more reactive and provide for substantial conversion with high selectivity to the product.

The quantity of antimony, bismuth or arsenic-containing compound is somewhat empirical and can vary widely depending upon the reactivity of the catalyst and the reactivity of the reactants present. Usually, though, the amount used to provide a catalytic effect ranges from about 0.01 to 20% mole percent based upon the amount of the alkylenediamine compound present in the reaction mixture, and preferably in an amount of from about 0.5 to 8 mole percent based on the amount of alkylene diamine compound. Within these ranges though, the level of catalyst again is somewhat empirical and is adjusted depending on the product state desired. It has been found that as the reactivity of the catalyst increases and conversion increases, selectivity is reduced. In those instances where there is substantial catalytic activity, then, the quantity of catalyst is reduced to increase selectivity with a concomitant reduction in conversion.

In the preparation of linear polyalkylene polyamines, and preferably the linear polyethylene polyamines, the reaction is maintained at a temperature of from about 225° to about 350° C., and preferably from about 275° to 300° C. The pressure utilized for carrying out the reaction is that sufficient to maintain the reaction in essentially liquid phase which normally ranges from about 800 to 2500 psig. When utilizing these temperatures and pressures, the reaction is allowed to proceed until a desired conversion is obtained or reaction is complete. Normally the reaction is carried out within about 1 to 2 hours.

It is important in carrying out the process that the proportion of alkylenediamine compound to alkanolamine compound, be in a stoichiometric excess, e.g. to 10:1, to result in highest selectivity to linear product. When the alkylene diamine compound approaches a 1:1 molar ratio with the alkanolamine, or falls below that level then the alkanolamine may have a tendency to form the cyclic amine compositions. Generally, the mole ratio of alkylenediamine compound to alkanolamine compound is from about 0.3 to 5.0, and preferably about 0.5 to 2.0.

Recovery of the linear polyalkylene polyamines from the reaction mixture can be accomplished by conventional techniques, these techniques generally involving a distillation reaction. Often a small amount of a salt, such as the one used as the catalytic material, is added to the polyalkylene polyamine separation purification as described in U.S. Pat. No. 3,755,447.

The following examples illustrate the nature of the process described herein that are not intended to limit the scope of the invention.

EXAMPLES 1-10

A series of runs were made to produce linear polyethylene polyamines by the reaction of ethylenediamine and ethanolamine in a mole ratio of 1:2 in the presence of various catalysts. The reaction was carried out in a 2 milliliter shaker reactor at a pressure of 1,000 psig and a temperature of 300° C. Each reaction was carried out for about two hours. At the completion of the reaction, the contents were cooled and the reaction mixture analyzed by gas-liquid chromatography.

Run 10 attempted to duplicate the art as taught by U.S. Pat. No. 4,036,881, which used boron phosphate as the catalyst. This was used for comparative purposes.

Tables 1 and 2 show results in terms of the amount of polyamines produced by the reaction. Conversion and selectivity are specified. As noted, the catalytic component was varied and the amount varied on the basis of weight mole percent of the alkylenediamine.

TABLE 1

POLYETHYLENE AMINES FROM ETHYLENEDIAMINE AND ETHANOLAMINE[a]

| RUN | CATALYST | LEVEL MOLE % | TEMP. °C. | PIP | TEDA | DETA | AEP | TAEA | TETA |
|---|---|---|---|---|---|---|---|---|---|
| 1 | Bismuth Nitrate | 2.5 | 300 | — | 0.36 | 5.51 | 3.55 | 0.19 | 1.75 |
| 2 | Arsenic Pentoxide | 2.5 | 300 | 8.56 | 1.02 | 9.6 | 9.65 | 0.47 | 1.68 |
| 3 | Arsenic Pentoxide | 2.5 | 325 | 7.21 | 1.20 | 5.76 | 7.29 | 0.72 | 1.36 |
| 4 | Ammonium Dihydrogen Phosphate | 2.5 | 325 | 6.63 | 0.78 | 6.55 | 6.46 | 0.23 | 0.37 |
| 5 | Phenylarsenic Acid | 2.5 | 325 | — | 0.53 | 2.34 | 0.79 | — | 0.19 |
| 6 | Bismuth Oxide | 2.5 | 325 | 5.19 | 0.78 | 3.05 | 2.54 | 0.07 | 0.37 |
| 7 | Bismuth Oxide | 2.5 | 325 | 3.32 | 0.4 | 3.12 | 2.62 | 0.16 | 0.32 |
| 8 | Antimony Oxide | 2.5 | 325 | 4.27 | 0.52 | 2.83 | 2.48 | 0.3 | 0.43 |
| 9 | Disodium Hydrogen Arsenate | 2.5 | 325 | — | 0.79 | 1.20 | 3.59 | 0.04 | 0.09 |
| 10 | Boron Phosphate | 5.0 | 300 | Prior Art | | | | | |

| RUN | CATALYST | LEVEL MOLE % | TEMP. °C. | BAEP | PEEDA | AE—TETA | TEPA | AE—BAEP | AE—PEEDA |
|---|---|---|---|---|---|---|---|---|---|
| 1 | Bismuth Nitrate | 2.5 | 300 | 3.67 | 2.05 | 34.14 | — | 4.07 | — |
| 2 | Arsenic Pentoxide | 2.5 | 300 | 3.7 | 2.7 | 16.28 | — | 2.75 | 0.21 |
| 3 | Arsenic Pentoxide | 2.5 | 325 | 3.25 | 3.38 | 12.89 | 0.25 | 4.74 | 0.35 |
| 4 | Ammonium Dihydrogen Phosphate | 2.5 | 325 | 2.27 | 1.6 | 11.54 | — | 4.09 | 0.23 |
| 5 | Phenylarsenic Acid | 2.5 | 325 | 0.8 | 0.6 | 3.77 | — | 0.29 | — |
| 6 | Bismuth Oxide | 2.5 | 325 | 0.62 | 0.63 | 3.09 | — | 0.57 | — |
| 7 | Bismuth Oxide | 2.5 | 325 | 1.08 | 0.81 | 2.31 | — | 1.29 | ' |
| 8 | Antimony Oxide | 2.5 | 325 | .09 | 0.65 | 2.31 | — | 2.58 | — |
| 9 | Disodium Hydrogen Arsenate | 2.5 | 325 | 0.70 | 0.98 | 4.87 | — | 0.44 | — |

TABLE 1-continued

POLYETHYLENE AMINES FROM ETHYLENEDIAMINE AND ETHANOLAMINE[a]

| | | | | |
|---|---|---|---|---|
| 10 | Boron Phosphate | 5.0 | 300 | Prior Art |

[a]All numbers refer to weight percent of individual components in the product mixture on a feedstock-free basis.
PIP — Piperazine
TEDA — Triethylene diamine
DETA — Diethylenetriamine
AEP — Aminoethylpiperazine
TAEA — Tris(aminoethyl)amine
TETA — Triethylenetetramine
BAEP — N,N[1]—Bis(aminoethyl)piperazine
PEEDA — N—(Piperazinoethyl)ethylenediamine
AE—TETA — N—(Aminoethyl)triethylenetetramine
TEPA — Teraethylenepentamine
AE—BAEP — N—(2-(2-aminoethylamino)-N[1]—(2-aminoethyl)piperazine
AE—PEEDA — N—(2-Piperazinoethyl)diethylenetriamine

TABLE 2

COMPARISON OF NITROGEN AND PHOSPHOROUS CATALYSTS

| Example | Catalyst | Level[a] | Conversion[b] | Selectivity[c] |
|---|---|---|---|---|
| 1 | Bismuth Nitrate | 2.5 | 52.0 | 75.2 |
| 2 | Arsenic Pentoxide | 2.5 | 68.8 | 43.3 |
| 3 | Arsenic Pentoxide | 2.5 | 59.9 | 45.8 |
| 4 | Ammonium Dihydrogen Arsenate | 2.5 | 59.9 | 45.8 |
| 5 | Phenylarsenic Acid | 2.5 | 48.2 | 67.7 |
| 6 | Bismuth Oxide | 2.5 | 35.5 | 38.9 |
| 7 | Bismuth Oxide | 2.5 | 49.4 | 38.3 |
| 8 | Antimony Oxide | 2.5 | 38.7 | 38.8 |
| 9 | Disodium Hydrogen Arsenate | 2.5 | 72.5 | 48.8 |
| 10 | Boron Phosphate | 5.0 | 94.9 | 31.0 |

[a]Mole percent of catalyst included, based on total amine feed.
[b]Weight percent of ethylenediamine and ethanolamine consumed in the reaction.
[c]Weight percent of noncyclic polyethylene amine products formed.

Tables 1 and 2 show that the antimony, bismuth, and arsenic containing catalysts were effective in producing a variety of linear polyalkylene polyamines. As compared to the prior art catalyst, boron phosphate, selectivity was slightly better in almost every case. Although conversions were not as high as with boron phosphate, conversions were good.

EXAMPLES 11-13

A series of runs similar to the previous examples were made to produce linear polyethylene polyamines by the reaction of ethylenediamine and ethanolamine except that a mole ratio of 1:1, was used in Runs 11-13. At the completion of the reaction, the contents were cooled and the reaction mixture analyzed by gas-liquid chromatography.

Run 13 corresponds to Example 9, which provides a comparison with only using 2.5 mole percent boron phosphate.

Tables 3 and 4 show results in terms of the amount of polyamines produced by the reaction.

TABLE 3

POLYETHYLENE AMINES FROM ETHYLENEDIAMINE AND ETHANOLAMINE[a]

| RUN | CATALYST | LEVEL MOLE % | TEMP. °C. | PIP | TEDA | DETA | AEP | TAEA | TETA |
|---|---|---|---|---|---|---|---|---|---|
| 11 | Arsenic Pentoxide | 2.5 | 325 | 1.43 | 0.1 | 0.28 | 0.94 | 0.38 | 0.4 |
| 12 | Ammonium Dihydrogen Arsenate | 5.0 | 325 | 1.34 | 0.6 | 1.85 | 0.2 | 0.06 | 0.97 |
| 13 | Boron Phosphate | 2.5 | 300 | Prior Art | | | | | |

| RUN | CATALYST | LEVEL MOLE % | TEMP. °C. | BAEP | PEEDA | AE—TETA | TEPA | AE—BAEP | AE—PEEDA |
|---|---|---|---|---|---|---|---|---|---|
| 11 | Arsenic Pentoxide | 2.5 | 325 | 0.76 | 0.75 | — | 1.08 | — | 0.22 |
| 12 | Ammonium Dihydrogen Phosphate | 5.0 | 325 | 0.3 | 0.3 | — | — | — | 0.11 |
| 10 | Boron Phosphate | 2.5 | 300 | Prior Art | | | | | |

[a]All numbers refer to weight percent of individual components in the product mixture on a feedstock-free basis.
PIP — Piperazine
TEDA — Triethylene diamine
DETA — Diethylenetriamine
AEP — Aminoethylpiperazine
TAEA — Tris(aminoethyl)amine
TETA — Triethylenetetramine
BAEP — N,N[1]—Bis(aminoethyl)piperazine
PEEDA — N—(Piperazinoethyl)ethylenediamine
AE—TETA — N—(Aminoethyl)triethylenetetramine
TEPA — Tetraethylenepentamine
AE—BAEP — N—(2-(2-aminoethylamino)-N[1]—(2-aminoethyl)piperazine
AE—PEEDA — N—(2-Piperazinoethyl)diethylenetriamine

TABLE 4

Comparison of Arsenic and Phosphate Catalysts - 1:1 Ethylenediamine: Ethanol Amine Ratio

| Example | Catalyst | Level[a] | Conversion[b] | Selectivity[c] |
|---|---|---|---|---|
| 11 | Arsenic Pentoxide | 2.5 | 54.6 | 33.8 |
| 12 | Ammonium Hydrogen Arsenate | 5.0 | 50.8 | 55.5 |
| 13 | Boron Phosphate | 2.5 | 84.8 | 26.8 |

[a]Mole percent of catalyst included, based on total amine feed.
[b]Weight percent of ethylenediamine and ethanolamine consumed in this reaction.
[c]Weight percent of noncyclic polyethylene amine products formed.

Again, the tables show that the arsenic salts provide good yields of polyethylene polyamines, and compare with the prior art boron phosphate. As compared to the results in Tables 1 and 2, it can be seen that conversion and selectivity decreased slightly for the same catalyst. Selectivity would be expected to decrease since the ethanolamine concentration is higher and it can react with itself to form cyclics.

What is claimed is:

1. A process for preparing a noncyclic polyalkylene polyamine comprising the steps of:

contacting an alkyleneamine compound having two primary amino groups of the formula:

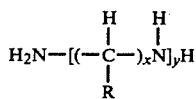

wherein R is hydrogen or a lower alkyl, X is a number from 2 to about 6, and Y is a number from 1 to about 4 with a hydroxy compound having primary or secondary hydroxyl groups of the general formula:

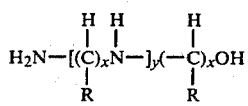

wherein R is hydrogen or a lower alkyl, X is a number from 2 to about 6; and Y is a number from 0 to about 3;

said contacting being performed in the presence of a catalytically effective amount of a compound containing bismuth, arsenic or antimony at temperatures sufficient to effect reaction between said alkyleneamine and said hydroxy compound under a pressure sufficient to maintain the reaction mixture essentially in liquid phase.

2. The process of claim 1 wherein said compound containing bismuth, arsenic or antimony is a salt.

3. The process of claim 2 wherein said salt is an arsenic containing salt.

4. The process of claim 1 wherein the level of said catalytic substance is from about 0.01 to 2.0 mole percent based upon the amount of said alkyleneamine compound present in the reaction mixture.

5. The process of claim 4 wherein the temperature of the reaction is from about 225° to 350° C.

6. The process of claim 5 wherein the molar ratio of alkyleneamine compound to hydroxy compound is from about 0:3 to about 5.

7. The process of claim 2 wherein said salt is an oxygen containing salt of antimony, bismuth, or arsenic.

8. The process of claim 7 wherein said salt is selected from the group consisting of arsenic petroxide, alkali metal arsenate, antimony oxide, and bismuth oxide.

* * * * *